United States Patent [19]

Chang

[11] Patent Number: 4,865,754
[45] Date of Patent: Sep. 12, 1989

[54] LUBRICANT OVERBASED PHENATE DETERGENT WITH IMPROVED WATER TOLERANCE

[75] Inventor: Yuehsiung Chang, Naperville, Ill.

[73] Assignee: Amoco Corporation, Chicago, Ill.

[21] Appl. No.: 120,829

[22] Filed: Nov. 16, 1987

Related U.S. Application Data

[63] Continuation of Ser. No. 818,863, Jan. 14, 1986, abandoned.

[51] Int. Cl.$^4$ ............................................. C10M 105/00
[52] U.S. Cl. .................................... 252/39; 252/42.7; 252/388; 252/48.2
[58] Field of Search ................. 252/39, 42.7, 33.2, 252/48.2, 388; 568/18, 19

[56] References Cited

U.S. PATENT DOCUMENTS

| | | | |
|---|---|---|---|
| 3,036,971 | 5/1962 | Otto | 252/42.7 |
| 3,923,670 | 12/1975 | Crawford | 252/42.7 |
| 4,221,673 | 9/1980 | Robson | 252/42.7 |
| 4,255,589 | 3/1981 | Wisotsky | 252/42.7 X |
| 4,282,106 | 8/1981 | Schaap | 252/39 X |
| 4,328,111 | 5/1982 | Watson | 252/42.7 X |
| 4,710,308 | 12/1987 | Stauffer | 252/42.7 |

*Primary Examiner*—William R. Dixon, Jr.
*Assistant Examiner*—James M. Hunter, Jr.
*Attorney, Agent, or Firm*—Matthew R. Hooper; William H. Magidson; Ralph C. Medhurst

[57] ABSTRACT

An improved overbased sulfurized alkaline earth metal phenate detergent lubricating oil additive and the process for its preparation are disclosed. The overbased sulfurized alkaline earth metal phenate detergent lubricating oil additive comprises the reaction product of an alkaline earth metal compound, sulfur, and an alkylphenol in the presence of a polyhydroxy compound and, an alkaline earth metal alkylbenzene sulfonate wherein the reaction mixture is carbonated with carbon dioxide. A lubricating oil composition comprising a major amount of a lubricating oil as base oil and a minor amount of said overbased sulfurized alkaline earth metal phenate detergent lubricating oil additive demonstrates improved storage at elevated temperatures, improved water tolerance and improved compatibility of the phenate-sulfonate mixture, particularly if water is present.

18 Claims, No Drawings

LUBRICANT OVERBASED PHENATE DETERGENT WITH IMPROVED WATER TOLERANCE

This is a continuation of application Ser. No. 818,863, filed Jan. 14, 1986 now abandoned.

FIELD OF THIS INVENTION

The field of this invention relates to a composition comprising an overbased detergent lubricant additive and to a process for the preparation of said overbased detergent additive useful as an additive for lubricating oils. More particularly, this invention relates to a process for the preparation of an overbased detergent additive having improved water tolerance in the finished lubricating oil.

It is an object of this invention to provide a process for the preparation of an overbased phenate which demonstrates improved storage at elevated temperatures, improved water tolerance and improved compatibility of the phenate-sulfonate mixture, particularly if water is present.

It is an object of this invention to provide a lubricant composition comprising an overbased detergent which has improved compatibility as an additive in a lubricating oil composition and good storage stability at elevated temperatures.

It is an object of this invention to provide a lubricant composition comprising an overbased detergent which has improved stability in a lubricating oil composition containing wear inhibitors comprising zinc dithiophosphate.

It is an object of this invention to provide a lubricant composition which has improved water tolerance and comprises an overbased phenate detergent.

These and other objects will become apparent from the description given hereafter.

BACKGROUND OF THIS INVENTION

Basic sulfurized calcium alkylphenates are used as compounding agents or additives in lubricating oils to neutralize harmful acids in internal combustion engines and to inhibit corrosion, gum formation and piston ring sticking caused by oxidation of the lubricating oil and oxidative polymerization of the engine fuel residues. Metal sulfonates are commonly used in lubricating oil compositions as additives, rust inhibitors and detergents. It is highly desirable for such phenates or sulfonates to provide neutralization capacity for acids formed in engine combustion without too rapid loss in alkalinity. In some cases, these compounding agents or additives are overbased, containing a molar excess of base over that needed to neutralize the phenolic material or sulfonic acid.

A problem associated with the preparation of overbased additive compounds is that of the incompatibility of the mixture of the alkaline earth metal phenate and the sulfonate as a final product. The overbased materials, generally an alkaline earth metal compound, generally a carbonate, are dispersed in the alkaline earth metal dispersing agent, the amount of dispersed alkaline earth metal being known as the overbased amount. Since the greater the basicity of the material the better, as this allows smaller amounts of the material to be used for a given effect in a lubricant, a greater degree of overbasing is highly desirable. However, to increase basicity, it is generally necessary to increase the dispersed alkaline earth metal content of the carbonate complex.

A highly desirable object of overbasing additive agents is to obtain the overbased additive agents in the form of extremely fine particles in a finely dispersed colloidal form such that the lubricant compositions containing the overbased additive agents are stable, are haze-free, are gelatin-free and are not subject to appreciable thickening.

The instant invented process relates to increased both carbonation and sulfurization of an alkaline earth metal phenate in the presence of a low-based sulfonate promoter to give a resulting product with improved water tolerance, due to overcoming incompatibility of the phenate and sulfonate.

Overbased phenates, including sulfurized phenates, are commonly manufactured in the presence of ethylene glycol which must be removed from the product. The presence of glycol in overbased phenates can cause engine varnish or lacquer. Phenates are generally the reaction product of phenol or substituted phenol with a metal or ammonium base. Often the metal base is a Group II metal compound. Substituted phenols are generally mono-, di- or tri-hydrocarbyl substituted, such as alkyl, alkenyl, aryl, aralkyl, or alkaryl. Monoalkyl substitution is preferred. The hydrocarbyl can comprise low molecular weight groups such as methyl, ethyl, the isomers of propyl, butyl, pentyl, hexyl, heptyl, octyl, nonyl, decyl and the like up to high molecular weight materials having a number average molecular weight of 10,000 or more. These hydrocarbyl substituents can be intermediate molecular weight polymer olefins such as $C_8$–$C_{100}$ ethylene or propylene or butene polymers. The hydrocarbyl can be substituted with groups such as chlorine, bromine, hydroxy, nitro or sulfonic acid groups so long as such substitution does not interfere with the utility of the composition. The Group II metal compound can comprise a metal oxide, hydroxide, alcoholate, acetate and the like. Common metals are calcium, barium, strontium and magnesium. Often, the metal compound is calcium oxide or hydroxide. Phenates can contain sulfur which can be introduced by reaction of elemental sulfur or $SCl_2$ with phenol or substituted phenol, or by reaction of elemental sulfur or $SCl_2$ with metal phenate.

Methods of making these various phenates and sulfur containing phenates and overbasing can be found in U.S. Pat. Nos. 2,680,096; 3,036,971; 3,178,368; 3,336,224; 3,437,595; 3,464,970; 3,761,414; 3,801,507; 3,810,837; 3,923,670; 3,932,289; 3,953,519; 3,966,621 and 3,969,235.

As is well-known, calcium phenates having TBN's of 80–250 tend to interact with low and high base sulfonates to produce haze and sediment when blended into crankcase oils. This phenate-sulfonate incompatibility can be influenced by the components in a finished oil. For example, the simultaneous presence of zinc dialkyldithiophosphate (ZnDTP) and water can aggravate the phenatesulfonate interaction. Many finished oils contain ZnDTP. This phenate-sulfonate incompatibility is worsened when the finished oil contains a small amount of water, as can happen during handling and storage.

It has long been known, as evidenced by U.S. Pat. Nos. 4,293,431; 4,302,342 and 4,412,927, that an overbased metallic detergent-dispersant can be prepared by carbonating a sulfurized alkylphenate of an alkaline earth metal, an alkaline-earth metal alkylbenzene sulfonate, an alkaline-earth metal compound, an alkylene glycol and a diluent oil. These approaches, however, utilize a significant amount (>20 wt % based on phenate) of sulfonate for the phenate overbasing reaction. This obviously reduces the effective reactor volume for the phenate reaction and the resulting product loses flexibilities in its applications.

In our process, we have found that only a small amount (<10 wt% and preferably <5 wt %) of low-based sulfonate is required as a promoter for alkaline earth metal phenate reactions in the presence of an alkylene glycol and a diluent oil. These sulfonate promoted phenates in an overbased state have improved solubility in lubricating oils, particularly in the presence of small amounts of water, are stable colloidal dispersions, are haze-free, are gelatin-free, non-viscous and are not subject to appreciable thickening. We have also found that optimization of both sulfurization and carbonation provides improved water tolerance in lubricating oil additives.

SUMMARY OF THE INVENTION

A process is disclosed for preparation of an overbased sulfurized calcium phenate with improved water tolerance and excellent storage stability. Finished lubricant oils containing this additive demonstrate continued brightness and clarity despite a water content of up to 0.20 wt %. The additive is prepared by reacting a mixture of an alkaline earth metal compound, sulfur and a polyhydroxy compound with an alkylphenol in the presence of an alkaline earth metal alkylbenzene sulfonate wherein the reaction mixture is carbonated with carbon dioxide. Both a high carbonation level and a high sulfurization level aid stability in the presence of water.

DETAILED DESCRIPTION OF THE INVENTION

It has been now found that the effectiveness of overbased sulfurized calcium alkylphenate as a lubricating oil additive can be enhanced by preparing the sulfurized calcium phenate in the presence of a low-based calcium sulfonate as a promoter wherein the mole ratios of the sulfur/calcium/glycol/carbon dioxide alkylphenol reactants and reaction parameters are critically controlled. The resulting product of the instant invention demonstrates an improved water tolerance when incorporated into a lubricating oil composition over the performance obtained with an overbased sulfurized calcium alkylphenate prepared in a conventional manner.

The overbased phenate with improved lubricating oil properties can be prepared by forming a calcium compound, alkylphenol and glycol intermediate in the presence of a low-base calcium sulfonate in a prereaction step before reacting the above compounds with sulfur to form a sulfurized calcium phenate. This prereaction step, as is taught in commonly-assigned Serial No. 754,647, filed July 12, 1985, reduces the formation of neutral calcium compounds and enhances the effectiveness of sulfurized calcium alkylphenate as a lubricating oil additive. Additional glycol is then added and the mixture is carbonated. The stripped product is filtered to remove solids.

The above process can be carried out by mixing the above first four compounds and heating the mixture for a period of from 10 up to 60 seconds at a temperature within the range of from about 300° F. to about 350° F. Heating the mixture for periods longer than 60 seconds causes the mixture to become less fluid and to form a heavy paste-like material. Heating the mixture for periods less than 10 seconds prevents the formation of a suitable reaction intermediate. Sulfur is then added to the reaction mixture which is heated at a temperature of from about 330° F. to about 370° F. for a period of from 1 to 2 hours. Additional glycol is then added and the mixture is carbonated with carbon dioxide for a period of from 1 to 2 hours at a temperature of from about 300° F. to about 360° F. Excess glycol and unreacted alkylphenol are then nitrogen-stripped from the reaction mixture at a temperature within the range of from about 470° F. to about 490° F. for a period of 0.5 to 1 hour. The stripped product is filtered to remove solids.

The above processing steps can be performed by either batch or continuous processing methods. However, for purposes of control of process parameters, it has been found advantageous to use a system of continuous processing. As indicated above, pretreatment of the glycol/calcium compound for periods longer than 60 seconds causes the resulting product to become difficult to pump; pretreatment for periods less than 10 seconds prevents formation of the chemical intermediates necessary for obtaining the required final product. Batch processing of the alkyl phenol/glycol/calcium compounds accordingly tends to result in a product exceedingly viscous and difficult to handle.

Although the above processing steps can be performed by either continuous or batch processing method, for purpose of illustration only, the following discussion is related to continuous processing. A schematic flow diagram of the continuous process is shown in FIG. 1. The mixture of an alkylphenol and lime is prereacted with glycol in the presence of low-base calcium sulfonate in a preheating section prior to the introduction of the sulfur. When the sulfur is introduced into the first reactor, water vapor and hydrogen sulfide gas are evolved. Carbon dioxide and additional glycol are introduced into the second reactor for the carbonation reaction. A reaction diluent is preferably provided so as to allow easy handling of the reaction products during the processing steps. After the reaction, the crude product is stripped to remove glycol and unreacted alkylphenol, then filtered to remove solids.

The alkylphenols useful in this invention are of the formula $R(C_6H_4)OH$ wherein R is a straight chain or branched chain alkyl group having from 8 to 40 carbon atoms and preferably from 10 to 30 carbon atoms, and the moiety $(C_6H_4)$ is a benzene ring. Examples of suitable alkyl groups are octyl, decyl, dodecyl, tetradecyl, hexadecyl, triacontyl, etc., up to tetracontyl.

The glycols used in the present invention can contain up to 6 carbon atoms. Suitable glycols include ethylene glycol; propylene glycol; butane diol-2,3; pentane diol-2,3; and 2-methylbutane diol-3,4. Ethylene glycol is the preferred glycol because of higher reaction yield.

The calcium compound can be either calcium oxide or calcium hydroxide. Calcium hydroxide, as hydrated line, is preferred for the continuous feeding. Other alkaline-earth metal compounds can also be used such as the oxides or hydroxides of barium, magnesium, strontium, etc., alone or in mixtures. However, it should be understood that the alkaline earth metal compounds are not equivalent for purposes of the present invention because, under certain conditions, some are more effective than others.

Among the low-base alkylbenzene sulfonates which can be used are the natural sulfonic acid salts of a molecular weight preferably of more than 400 obtained by sulfonation of petroleum cuts or synthetic salts obtained by sulfonation of alkylbenzenes derived from olefins or polymers of $C_2$–$C_4$ olefins of chain length $C_{15}$–$C_{80}$ and alkaline earth metals such as calcium, barium, magnesium, etc. A low-base calcium sulfonate prepared from a polypropene of about C-60 chain length is preferred.

The reaction diluent can be any lubricating oil such as would be used in the final lubricating oil formulation. These lubricating oils include naphthenic base, paraffin base, and mixed base mineral oils and other hydrocarbon lubricants such as synthetic lubricating oils and lubricating oil derived from coal products.

The mole ratios of the reactants are critical. Although the mole ratios of glycol to calcium can vary slightly, it is preferred that the mole ratio of glycol in the reactant mixture be about equal to that of the calcium hydroxide. Although there is no maximum as to the amounts of sulfur and carbon dioxide used, as a practical matter, a maximum of 2 moles each of sulfur and carbon dioxide per mole of alkylphenol is adequate. The reaction stoichiometry, including the reaction diluented, e.g., a hydrocarbon such as a 5W petroleum oil, is as follows:

|  | Range | Preferred Range |
|---|---|---|
| Lime; moles/mole alkylphenol | 0.7–1.7 | 0.9–1.2 |
| Sulfur: moles/mole alkylphenol | 1.1–2.0 | 1.3–1.6 |
| Glycol: moles/mole alkylphenol | 0.7–1.7 | 0.9–1.3 |
| Low-base Calcium Sulfonate, lbs/lb-mole alkylphenol | 2.5–30 | 5–15 |
| Carbon Dioxide: moles/mole alkylphenol | 0.5–2.0 | 0.5–1.5 |
| 5W Oil; lbs/lb-mole alkylphenol | 100–500 | 150–300 |

The temperatures at which the reactants will react in the prereaction between the glycol and line in the presence of the alkylphenol are dependent upon the nature of the reactants. Ethylene glycol, dodecylphenol and lime prereaction mixtures will react to form a suitable reaction intermediate at 300° F. to 350° F. at atmospheric pressure. The reaction intermediate and sulfur are reacted at 330° F. to 370° F. for a nominal residence time of from 1 to 2 hours and at 300° F. to 360° F. for an additional 1 to 2 hours at atmospheric pressure during which glycol is added and the mixture is carbonated. Although the reactions take place at atmospheric pressure, pressures less or greater than atmospheric can also be used.

An essential element of the invention is the ratio of the carbonate total base number (TBN) as measured by coulometric titration and the total TBN (ASTM D-2896) relative to the sulfur to calcium weight ratio as determined by x-ray fluorescence. In the coulometric method, an excess amount of hydrochloric acid is added to the sample to release carbon dioxide from the sample. The released carbon dioxide is then titrated potentiometrically. The method measures the amount of inorganic carbonates present. The ASTM D-2896 test method has been developed to measure the basicity of strongly overbased oil additives by titration with perchloric acid and does measure the basicity caused by components such as calcium carbonate.

The chemistry of the reactions involved in the process of the instant invention is quite obscure. It is not desired to be bound by any particular theory or hypothesis as to what occurs during the preparation of the overbased sulfurized alkaline earth metal phenate detergent of the instant invention to prepare a finished detergent with improved storage capability at higher temperatures and improved water tolerance. However, it has unexpectedly been found that increased carbonation and sulfurization in the presence of a low-based sulfonate promoter results in an improved overbased sulfurized alkaline earth metal phenate detergent wherein the said phenate detergent has measurable characteristics as determined by coulometric titration, the D-2896 method and x-ray fluorescence weight determination of sulfur and calcium present.

Use of the above suitable analytical techniques developed the data presented hereinafter in Example IV and represented in FIG. 2. As is evident in FIG. 2, water tolerance of the phenate detergent composition of the instant invention is improved when the nitrogen stripped product of the instant invention has coulometric titration carbonate TBN to total TBN (ASTM D-2896) ratio of at least 0.35 when the sulfur to calcium weight ratio is at least 0.52 and said coulometric titration carbonate TBN to total TBN (ASTM D-2876) ratio is at least 0.57 when said sulfur to calcium weight ratio is at least 0.38

The overbased calcium phenate prepared above is blended with other additives to form a so-called additive package at a temperature within the range of from about 160° F. to about 275° F. or higher under nitrogen for 1 to 24 hours, at pressures of from 0.5 to 100 atmospheres. Additive blends containing thermally unstable additives such as zinc dithiophosphate can be blended at 160° F. for about three hours.

Of particular significance, in accordance with the present invention, is the ability to improve the storage properties of compositions of overbased detergent-dispersants and oleaginous materials such as lubricating media which may comprise either a mineral oil or a synthetic oil. In general, mineral oils, both paraffinic, naphthenic and mixtures thereof, employed in the lubricant viscosity range, as for example, from about 45 SSU at 100° F. to about 6000 SSU at 100° F., and preferably, from about 40 to about 250 SSU at 210° F. These oils may have viscosity indexes ranging to about 100 or higher. Viscosity indexes from about 70 to about 95 are preferred. The average molecular weights of these oils may range from about 250 to about 800.

In instances where synthetic oils are desired in preference to mineral oils, or in combination therewith, various compounds of this type may be successfully utilized. Typical synthetic vehicles include polyisobutylene, polybutenes, hydrogenated polyolefins, polypropylene glycol, polyethylene glycol, trimethylol propane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated mineral oils, chain-type polyphenyls, siloxanes and silicones (polysiloxanes), alkyl-substituted diphenyl esters typified by a butyl-substituted bis (p-phenoxy phenol) ester, phenoxy phenylesthers.

The term lubricating oil composition as used herein is meant to refer to fully formulated compositions intended for use, such as crankcase motor oils, which contain a major portion of a base oil as a lubricating oil and a number of conventionally used additives in typical amounts to provide their normal attendant functions, especially detergents and dispersants of the ash-producing or ashless type, oxidation inhibitors, rust inhibitors, viscosity index improvers, e.g., olefin copolymers, pour point depressants, and metal-containing detergent additives, such as neutral and basic metal phenates, sulfurized phenates and sulfonates with calcium and magnesium, such as a high-base magnesium sulfonate, and zinc dialkyldithiophosphates as anti-oxidant and wear inhibitor additives.

It is understood, therefore, that the lubricant oil compositions contemplated herein can contain other materials. For example, corrosion inhibitors, rust inhibitors such as magnesium sulfonate, nitrogen-containing dispersants, extreme pressure agents, viscosity index improvers, co-antioxidants, anti-wear agents such as zinc dialkyldithiophosphate and the like can be used. These materials do not detract from the value of the compositions of this invention, but rather they serve to impart their customary properties to the particular compositions in which they are incorporated.

In general, the overbased detergent of the present invention can be employed in any amount which is effective for imparting the desired degree of improved storage at room temperature or at elevated temperatures. In many applications, however, the overbased detergent is effectively employed in amounts from about 0.5% to about 15% by weight, and preferably from about 0.5 to about 5% of the total weight of the composition.

In summary, the instant invented process comprises a method for preparing an improved overbased sulfurized alkaline earth metal phenate detergent lubricating oil additive with improved storage stability at elevated temperatures and improved water tolerance which comprises: (a) reacting an alkaline earth metal compound with an alkylphenol in the presence of a polyhydroxy compound and an alkaline earth metal alkylbenzene sulfonate at a temperature within the range of from about 300° F. to about 350° F. for a period sufficient to effect a chemical reaction to form a reaction intermediate, (b) adding elemental sulfur to the reaction mixture of (a), (c) heating the reaction mixture of (b) at a temperature within the range of from about 330° F. to about 370° F. for a period sufficient to effect a reaction between said sulfur and said reaction mixture of (b), (d) adding an additional amount of said polyhydroxy compound to the reaction product of (c) to form a reaction mixture, (e) heating and carbonating said reaction mixture of (d) with carbon dioxide at a temperature within the range of from about 300° F. to about 360° F. for a period sufficient to obtain a high carbonation level of said reaction mixture of (d), (f) nitrogen-stripping said reaction mixture of (e) at a temperature within the range of from about 470° F. to about 490° F., (g) filtering the nitrogen-stripped product of (f) whereby said nitrogen-stripped product has a carbonate total base number (TBN) by coulometric titration to total TBN (ASTM D-2896) ratio of at least 0.35 when the sulfur to calcium weight ratio is at least 0.52, and said carbonate TBN by coulometric titration to total TBN (ASTM D-2896) ratio is at least 0.57 when said sulfur to calcium weight ratio is at least 0.38.

In summary, the instant invented compositions comprise an improved overbased sulfurized alkaline earth metal phenate detergent lubricating oil additive composition prepared by the hereinabove described invented process, and a lubricating oil composition containing a lubricating oil and an additive effective amount of the said improved overbased sulfurized alkaline earth metal phenate detergent lubricating oil additive.

The following examples are illustrative of typical compositions of the instant invention and of methods of preparing them. Percentages shown are weight percentages unless otherwise stated.

EXAMPLE 1

This example illustrates a batch preparation of an overbased detergent dispersant of the instant invention. To a one-liter resin kettle there was charged 210.0g dodecylphenol, 41.4g lime, 30.0g glycol, 10.0 $C_{60}$- calcium sulfonate, and 184.0g 5W oil. The mixture was stored and heated to 300° F. and held for a period of 60 seconds. At this point, 33.5 g sulfur was added and the mixture was heated to 360° F. with stirring and held for 60 minutes. The temperature was then allowed to decrease to 340° F. and 20.0 g glycol and 20.7g lime were added to the kettle. The mixture was then held at 340° F. for 120 minutes during which the mixture was carbonated with 0.2 liter/minute of carbon dioxide. The temperature was raised to 480° F. The mixture was then stripped with 0.3 liter/minute of nitrogen under a vacuum of 75 torr for 60 minutes. After addition of 40.0 g 5W oil to the reaction mixture, the product was filtered with 40.0 g Celite in a Buchner funnel. The sample number was 9745-149-1.

The product inspections are summarized below:

| Analyses | 9745-149-1 |
| --- | --- |
| Calcium, wt % | 6.5 |
| Sulfur, wt % | 3.0 |
| Glycol, wt % | 0.2 |
| D-2896 TBN, mg KOH/gm | 171 |
| Carbonate TBN[1], mg KOH/gm | 85 |
| PM Flash, °F. (Penske-Martin) | 372 |
| Viscosity, cSt at 100° C. | 65 |
| Residual Reaction Solids, vol % | <0.05 |
| Color, Double Dilute (ASTM-D-1500) | 3.0 |
| Gravity, lbs/gal | 8.5 |

[1]Per coulometric titration.

EXAMPLE II

The following example illustrates a continuous process preparation of an overbased detergent composition of the instant invention.

Two stirred four-liter resin kettles in series were used. Product stripping and filtration were batchwise and similar to those described in Example I. The reaction conditions are summarized below:

| | Moles/Mole Dodecylphenol |
| --- | --- |
| Lime | 1.00 |
| Sulfur | 1.43 |
| Glycol - 1st Reactor | 0.51 |
| 2nd Reactor | 0.63 |
| Total | 1.14 |
| Carbon Dioxide | 1.27 |
| C60- Calcium Sulfonate, lbs/mole | 12.5 |
| 5W Oil, lbs/mole | 242 |

| | Preheater | 1st Reactor | 2nd Reactor |
| --- | --- | --- | --- |
| Residence Time, min | 0.5 | 90 | 90 |
| Temperature, °F. | 330 | 360 | 340 |

The product inspections are summarized below:

| Analyses | 9226-38 |
| --- | --- |
| Calcium, wt % | 6.6 |

-continued

| Analyses | 9226-38 |
|---|---|
| Sulfur, wt % | 3.1 |
| Glycol, wt % | 0.3 |
| D-2896 TBN, mg KOH/gm | 173 |
| Carbonate TBN[(1)], mg KOH/gm | 82 |
| PM Flash, °F. (Penske-Martin) | 365 |
| Viscosity, cSt at 100° C. | 70 |
| Residual Reaction Solids, vol % | <0.05 |
| Color, Double Dilute (ASTM D-1500) | 3.0 |
| Gravity, lbs/gal | 8.6 |

[(1)]Per coulometric titration.

EXAMPLE III

The products of Examples I and II were blended into a heavy duty lubricating oil composition. The formulations were contained a nitrogen-containing dispersant, a zinc dialkyldithiophosphate wear inhibitor, a high-base magnesium sulfonate, a pour point depressant and a base oil. The control contained a overbased phenate prepared by conventional procedures. Several commercial overbased phenate samples, Oloa-218A, Oloa-219, and Oloa-229 available from Chevron Chemical Company, San Francisco, California, LZ-6599 and LZ-6500 available from Lubrizol Corp., Wickcliffe, Ohio, and Paranox-52 available from Exxon Chemical Co., Houston, Texas, were also blended into the heavy duty lubricating oil formulation based on their calcium contents. The water tolerance of the formulated portages was tested at 0.2 wt% at 70° F. and 130° F. for 30 days. The results were as follows:

|  | Water Tolerance (1) | |
|---|---|---|
|  | 70° F. | 130° F. |
| Control | N-6% | >N-7% |
| Sample 9745-149-1 | A-0% | A-0% |
| Sample 9226-38 | A-0% | A-0% |
| Oloa-218A | >N-5% | K-6% |
| Oloa-219 | >N-28% | >N-19% |
| Oloa-229 | J-20% | N-28% |
| LZ-6499 | >N-10% | I-11% |
| LZ-6500 | M-8% | N-7% |
| Paranox-52 | >N-1% | D-20% |

(1) Haze rating: A - clear, B to N - increased haze. Sediment is in volume %.

EXAMPLE IV

Because of the critical reaction stoichiometry, it is preferred to monitor the reaction process with suitable analytical techniques. This example illustrates that regulating the sulfurization and carbonation of phenate improves the water tolerance.

Thirty-one samples were prepared with different degrees of sulfurization and carbonation either by the batch process (9745 series shown in Table I) or by the continuous process (9226 series shown in Table I). Each sample was blended at 2.5 wt% into a heavy-duty lubricating oil composition and then mixed with 0.20% of water. The heavy-duty lubricating oil composition contained a nitrogen-containing dispersant, a zinc dialkyldithio-phosphate wear inhibitor, a high-base magnesium sulfonate, a pour-point depressant and base oil. The sample were stored at room temperature (70° F.) and 130° F. for 30 days. The water tolerance results are summarized in Table 1.

As the above table indicates, increased levels of sulfurization and carbonation improve water tolerance. These effects are more evidently illustrated in FIG. 2 which is a graphical representation of the data shown in Table I.

TABLE I

Haze and Sediment Upon a 30-Day Storage with 0.2 Wt. % Water

| Sample | S/Ca | Carbonate TBN (1) Total TBN (2) | Haze and Sediment (3) 70° F. | 130 F. |
|---|---|---|---|---|
| 9745-92-2 | 0.48 | 0.27 | >N-4% | >N-4% |
| -93-2 | 0.44 | 0.45 | I-2% | K-3% |
| -94-2 | 0.46 | 0.46 | K-1% | K-1% |
| -96-2 | 0.47 | 0.44 | | |
| -97-1 | 0.45 | 0.44 | E-1% | G-2% |
| -97-2 | 0.43 | 0.57 | | |
| -98-1 | 0.52 | 0.46 | | |
| -98-2 | 0.52 | 0.46 | | |
| -99-1 | 0.41 | 0.55 | | |
| -99-2 | 0.45 | 0.44 | D-1% | F-1% |
| -100-1 | 0.51 | 0.51 | | |
| -100-2 | 0.51 | 0.47 | | |
| -101-1 | 0.41 | 0.52 | | |
| -101-2 | 0.38 | 0.51 | >N-5% | >N-6% |
| -102-1 | 0.47 | 0.48 | | |
| -102-2 | 0.44 | 0.42 | C-0% | F-1% |
| -103-1 | 0.45 | 0.45 | B-0% | F-1% |
| -103-2 | 0.45 | 0.32 | >N-6% | >N-5% |
| -104-1 | 0.38 | 0.58 | >N-2% | >N-4% |
| -104-2 | 0.39 | 0.55 | >N-3% | >N-1% |
| -128-2 | 0.48 | 0.52 | | |
| -129-2 | 0.39 | 0.52 | | |
| -130-2 | 0.51 | 0.43 | | |
| -131-2 | 0.43 | 0.53 | | |
| -139-2 | 0.47 | 0.50 | | |
| -146-1 | 0.43 | 0.52 | | |
| -146-2 | 0.41 | 0.55 | | |
| -147-2 | 0.41 | 0.54 | | |
| -147-2 | 0.41 | 0.54 | | |
| 9226-35-2 | 0.49 | 0.52 | | |
| -35-3 | 0.50 | 0.39 | >N-1% | >N-5% |

(1) Per coulometric titration per ASTM D-664.
(2) Per ASTM D-2896 titration with perchloric acid.
(3) indicates clear and no sediment in mixture resulting from component used. Haze rating: A - clear, B to N - increased haze. Sediment is in volume %.

What is claimed is:

1. A process for preparing an improved overbased calcium phenate detergent lubricant oil additive with improved storage at elevated temperatures and improved water tolerance which comprises:

(a) reacting a calcium compound with an alkylphenol in the presence of a polyhydroxy compound and a calcium alkyl-benzene sulfonate at a temperature within the range of from about 300° F. to about 359° F. for a period sufficient to effect a chemical reaction intermediate, wherein the mole ratio of calcium compound to alkylphenol is about .7 to 1.7:1; and the amount of calcium alkylbenzene sulfonate is about 2.5–30 lbs per mole of alkylphenol;

(b) adding to the reaction mixture of (a) about 1.1 to 2.0 moles of elemental sulfur per mole of alkylphenol;

(c) heating the reaction mixture of (b) at a temperature within the range of from about 330° F. to about 370° F. for a period sufficient to effect reaction between said sulfur and said reaction mixture of (b);

(d) adding an additional amount of said polyhydroxy compound to the reaction product of (c) to form a reaction mixture;

(e) heating and carbonating the reaction mixture of (d) with about .5 to 2.0 moles of carbon dioxide per mole of alkylphenol at a temperature within the range of from about 300° F. to about 360° F.;

(f) nitrogen stripping the reaction product of (e) at a temperature within the range of from about 470° F. to about 490° F.; and (g) filtering the nitrogen-stripped product of (f); provided, first that the mole ratio of polyhydroxy compound to alkylphenol added in steps (a) and (b) shall be in the range of about .7–1.7 to 1; secondly, that the ratio of carbonate TBN to total TBN and the weight ratio of sulfur to calcium, are controlled such that the measured values of the said ratios in the nitrogen stripped product satisfy the equation $y \geq -1.5(x) + 1.14$ where y represents the ratio of carbonate TBN to total TBN, and x represents the weight ratio of sulfur to calcium such that the product results in a haze rating of A and sediment of 0 volume percent when the product is present for 30 days at 130° F. in a lubricant package comprising .2 wt.% water; and thirdly, said carbonate TBN to total TBN ratio having a value of at least .42 and said weight ratio of sulfur to calcium having a value of at least about .39.

2. The process of claim 1 wherein said polyhydroxy compound is selected from the group consisting of ethylene glycol, propylene glycol; butane diol-2,3; pentane diol-2,3; and 2-methylbutane diol-3,4.

3. The process of claim 1 wherein said polyhydroxy compound is ethylene glycol.

4. The process of claim 1 wherein said alkylphenol is of the formula $R(C_6H)OH$ wherein R is a straight claim or branched chain alkyl group having from 8 to 40 carbon atoms.

5. The process of claim 1 wherein said alkylphenol is selected from the group consisting of octylphenol, decylphenol, dodecylphenol, tetradecylphenol, hexadecyl phenol, triacontylphenol and tetracontylphenol.

6. The process of claim 1 wherein said alkylphenol is dodecylphenol.

7. The process of claim 1 wherein said calcium compound is selected from the group consisting of calcium oxide and calcium hydroxide.

8. The process of claim 1 wherein said calcium compound is calcium hydroxide.

9. The process of claim 1 wherein said calcium alkylbenzene sulfonate is a low base calcium sulfonate prepared from a polypropene of about 60 carbon atoms.

10. The process of claim 1 wherein the mole ratio of said polyhydroxy compound to said alkylphenol is in the range of from about .9 to 1.3:1.

11. The process of claim 1 wherein the mole ratio of said sulfur to said alkylphenol is in the range of from about 1.3 to 1.6:1.

12. The process of claim 1 wherein said calcium compound is lime and wherein the ratio of lime to alkylphenol is in the range of from about .9 to 1.2:1.

13. The process of claim 1 wherein the mole ratio of said carbon dioxide to said alkylphenol is in the range of from about .5 to 1.5:1.

14. The process of claim 1 wherein said calcium alkylbenzene sulfonate is present in the ratio of from about 5 to 15 lbs. per mole of alkylphenol.

15. The process of claim 1 wherein a reaction diluent is added in step (a) in a ratio of from about 100 to bout 500 lbs per mole of alkylphenol.

16. The process of claim 1 wherein said process is a batch process.

17. The process of claim 1 wherein said process is a continuous process.

18. The process of claim 1 wherein said polyhydroxy compound is ethylene glycol, said alkaline earth metal compound is calcium hydroxide, said alkylphenol is dodecylphenol, said sulfur is elemental sulfur, said alkaline earth metal alkylbenzene sulfonate is a low-base calcium sulfonate prepared from a polypropene of about C-60 chain length and said process is continuous.

* * * * *

UNITED STATES PATENT OFFICE
CERTIFICATE OF CORRECTION

Patent No. 4,865,754  Dated September 12, 1989

Inventor(s) Yuehsiung Chang

It is certified that error appears in the above-identified patent and that said Letters Patent is hereby corrected as shown below:

| Col. | Line | |
|---|---|---|
| 9 | 24 | "6599" and should read --6499-- |
| 11 | 29 | "R($C_6$H)OH and should read --R($C_6H_4$)OH-- |

Signed and Sealed this

Third Day of July, 1990

*Attest:*

HARRY F. MANBECK, JR.

*Attesting Officer*  *Commissioner of Patents and Trademarks*